United States Patent
Brunn et al.

(10) Patent No.: US 10,945,936 B2
(45) Date of Patent: Mar. 16, 2021

(54) AQUEOUS SURFACTANT COMPOSITIONS

(71) Applicant: BASF SE, Ludwigshafen am Rhein (DE)

(72) Inventors: Claudia Brunn, Düsseldorf-Holthausen (DE); Ansgar Behler, Düsseldorf-Holthausen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 16/301,505

(22) PCT Filed: May 11, 2017

(86) PCT No.: PCT/EP2017/061263
§ 371 (c)(1),
(2) Date: Nov. 14, 2018

(87) PCT Pub. No.: WO2017/198525
PCT Pub. Date: Nov. 23, 2017

(65) Prior Publication Data
US 2019/0290569 A1  Sep. 26, 2019

(30) Foreign Application Priority Data
May 18, 2016 (EP) .................................. 16170199

(51) Int. Cl.
| | | |
|---|---|---|
| *A61K 8/00* | (2006.01) | |
| *A61K 8/46* | (2006.01) | |
| *A61K 8/42* | (2006.01) | |
| *A61Q 5/02* | (2006.01) | |
| *A61Q 9/02* | (2006.01) | |
| *A61Q 19/10* | (2006.01) | |
| *C11D 1/655* | (2006.01) | |
| *C11D 1/04* | (2006.01) | |

(Continued)

(52) U.S. Cl.
CPC ............... *A61K 8/463* (2013.01); *A61K 8/42* (2013.01); *A61K 8/46* (2013.01); *A61Q 5/02* (2013.01); *A61Q 9/02* (2013.01); *A61Q 19/10* (2013.01); *C11D 1/655* (2013.01); *A61K 2800/596* (2013.01); *C11D 1/04* (2013.01); *C11D 1/12* (2013.01); *C11D 1/123* (2013.01); *C11D 1/28* (2013.01)

(58) Field of Classification Search
None
See application file for complete search history.

(56) References Cited

U.S. PATENT DOCUMENTS 2,195,088 A * 3/1940 Keppler ............... C07C 309/07
562/109
6,172,026 B1 * 1/2001 Ospinal ................ C11D 1/37
510/152

(Continued)

FOREIGN PATENT DOCUMENTS

DE         4220580 A1   1/1994
WO    WO-92/15660 A1   9/1992
(Continued)

OTHER PUBLICATIONS

Stepan Company USA, "Stepan's Cocamide DEA Replacements for Personal Care: Innovative Chemical Solutions for a Cleaner, Healthier, More Energy Efficient World," pp. 1-8, Oct. 1, 2015. [Online]. Available: https://www.stepan.com/uploadedFiles/Literature_and_Downloads/General_Lit/Personal_Care/StepanCocamideDEAReplacementsPersonalCare.pdf. [Retrieved on Sep. 16, 2016].

(Continued)

*Primary Examiner* — Necholus Ogden, Jr.
(74) *Attorney, Agent, or Firm* — Marshall, Gerstein & Borun LLP

(57) ABSTRACT

Aqueous surfactant compositions containing
  one or more alpha-sulfo fatty acid disalt (A) of general formula (I),

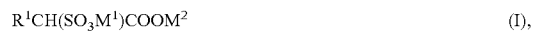

in which the radical $R^1$ is a linear or branched alkyl or alkenyl radical having 6 to 18 carbon atoms and the radicals $M^1$ and $M^2$, independently of one another, are selected from the group consisting of H, Li, Na, K, Ca/2, Mg/2, ammonium, and alkanolamine,
  one or more alkanolamide (B) selected from the group of compounds of general formula (IIa), (IIb) and (IIc),

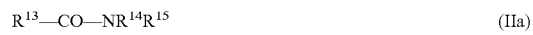

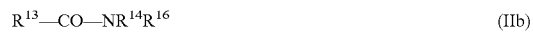

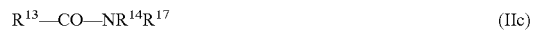

wherein the radical $R^{13}$ in compounds (IIa) is a linear or branched alkyl radical having 6 to 18 carbon atoms and the radicals $R^{14}$ and $R^{15}$, independently of each other, are a linear or branched hydroxyalkyl group having 1 to 4 carbon atoms;
  wherein the radical $R^{13}$ in compounds (IIb) is a linear or branched alkyl radical having 6 to 18 carbon atoms, the radical $R^{14}$ is a linear or branched hydroxyalkyl group having 1 to 4 carbon atoms and the radical $R^{16}$ is hydrogen;
  and wherein the radical $R^{13}$ in compounds (IIc) is a linear or branched alkyl radical having 6 to 18 carbon atoms, the radical $R^{14}$ is a linear or branched hydroxyalkyl group having 1 to 4 carbon atoms and the radical $R^{17}$ is an alkyl group having 1 to 4 carbon atoms; and
  water,
are disclosed. These compositions have good foaming ability, pleasant sensory properties of the foam, good skin compatibility, and are suitable for cosmetic agents as well as detergents and cleaners.

8 Claims, No Drawings

(51) Int. Cl.
*C11D 1/12* (2006.01)
*C11D 1/28* (2006.01)

(56) References Cited

U.S. PATENT DOCUMENTS

| | | | |
|---|---|---|---|
| 2005/0153853 A1* | 7/2005 | Sajic | C11D 17/006 510/141 |
| 2006/0257439 A1 | 11/2006 | Sabnis et al. | |
| 2009/0227482 A1* | 9/2009 | Dong | A61Q 5/02 510/125 |
| 2014/0076344 A1* | 3/2014 | Doi | A61Q 19/10 132/202 |
| 2017/0283741 A1 | 10/2017 | Behler et al. | |
| 2018/0119002 A1* | 5/2018 | Back | E21B 43/16 |

FOREIGN PATENT DOCUMENTS

| | | |
|---|---|---|
| WO | WO-2015/006300 A1 | 1/2015 |
| WO | WO-2015/117842 A1 | 8/2015 |
| WO | WO-2016/030172 A1 | 3/2016 |

OTHER PUBLICATIONS

International Search Report for Patent Application No. PCT/EP2017/061263, dated Aug. 4, 2017.
European Search Report for EP Patent Application No. 16170199.0, dated Sep. 28, 2016.

\* cited by examiner

AQUEOUS SURFACTANT COMPOSITIONS

CROSS-REFERENCE TO RELATED APPLICATIONS

This is a U.S. national phase of International Application No. PCT/EP2017/061263, filed May 11, 2017, which claims the benefit of European Patent Application No. 16170199.0, filed May 18, 2016.

FIELD OF THE INVENTION

The present invention relates to aqueous surfactant compositions with a content of alpha-sulfo fatty acid disalts and alkanolamides.

PRIOR ART

Anionic surfactants are some of the most widespread interface-active compounds and, apart from being used in detergents and cleaners, are also used for diverse purposes in the field of cosmetics. Customary anionic surfactants as are used in particular in cosmetics are the salts of alkyl ether sulfates (alkyl polyether sulfates, fatty alcohol polyglycol ether sulfates, in short also ether sulfates). They are characterized by a strong foaming ability, high cleaning power, low sensitivity to hardness and grease and are used widely for producing cosmetic products such as, for example, hair shampoos, foam or shower baths, but also in hand dishwashing detergents.

For many current applications, apart from a good interface-active effect, further requirements are placed on anionic surfactants. A high dermatological compatibility is required in particular in cosmetics. In addition, good foaming ability and a pleasant sensory property of the foam is generally desired. Furthermore, there is a need for anionic surfactants which can be produced at least partially from biogenic sources and specifically also renewable raw materials.

WO-A-92/15660 discloses liquid cleaners with a content of sulfo-oleic acid disalts. It is disclosed that sulfo-oleic acid disalts are able to reduce the viscosity of surfactants or surfactant mixtures for cleaners—particularly those based on fatty alkyl sulfates, fatty alkyl ether sulfates, alkylpolyglucosides and fatty acid monoethanolamides—and indeed just as effectively or even better than by adding ethanol or hydrotropes (page 2, second paragraph).

DESCRIPTION OF THE INVENTION

The object of the present invention was to provide aqueous surfactant compositions which are characterized by the properties specified below:
good foaming ability.
pleasant sensory property of the foam.
good skin compatibility.
The invention firstly provides aqueous surfactant compositions comprising
one or more alpha-sulfo fatty acid disalts (A) of general formula (I),

in which the radical $R^1$ is a linear or branched alkyl or alkenyl radical with 6 to 18 carbon atoms and the radicals $M^1$ and $M^2$—independently of one another—are selected from the group comprising H, Li, Na, K, Ca/2, Mg/2, ammonium and alkanolamines, one or more alkanolamides (B) selected from the group of compounds of general formula (IIa), (IIb) and (IIc),

  (IIa)

  (IIb)

  (IIc)

wherein the radical $R^{13}$ in compounds (IIa) is a linear or branched alkyl radical having 6 to 18 carbon atoms and the radicals $R^{14}$ and $R^{15}$—independently of each other—are a linear or branched hydroxyalkyl group having 1 to 4 carbon atoms;

wherein the radical $R^{13}$ in compounds (IIb) is a linear or branched alkyl radical having 6 to 18 carbon atoms, the radical $R^{14}$ is a linear or branched hydroxyalkyl group having 1 to 4 carbon atoms and the radical $R^{16}$ is hydrogen;

and wherein the radical $R^{13}$ in compounds (IIc) is a linear or branched alkyl radical having 6 to 18 carbon atoms, the radical $R^{14}$ is a linear or branched hydroxyalkyl group having 1 to 4 carbon atoms and the radical $R^{17}$ is an alkyl group having 1 to 4 carbon atoms;

water, where the following provisos apply:
with regard to compounds (A) it is the case that the fraction of the compounds (A) in which the radical $R^1$ is an alkenyl radical—based on the total amount of the compounds (A) in the aqueous surfactant compositions—is 3% by weight or less;

with regard to compounds (A) it is the case that the fraction of the compounds (A) in which the radical $R^1$ is a decyl or dodecyl radical—based on the total amount of the compounds (A)—is 70% by weight or more;

if the aqueous surfactant compositions comprise one or more ester sulfonates (E) of general formula (V),

  (V)

in which the radical $R^2$ is a linear or branched alkyl or alkenyl radical having 6 to 18 carbon atoms and the radical $R^3$ is a linear or branched alkyl or alkenyl radical having 1 to 20 carbon atoms, where the radical $R^3$ can logically be an alkenyl radical or be branched only above 3 carbon atoms, and the radical $M^7$ is selected from the group comprising Li, Na, K, Ca/2, Mg/2, ammonium and alkanolamines, it is the case that the compounds (A)—based on the totality of the compounds (A) and (E)—must be present to an extent of 50% by weight or more—and in particular to an extent of 90% by weight or more.

The aqueous surfactant compositions according to the invention are characterized by the following advantageous properties:

Good foaming ability and pleasant sensory property of the foam. In this regard, it may be noted that particularly in the field of cosmetics, foaming ability can be understood to mean different aspects, for example it being possible to use both foam volume, foam stability, foam elasticity, water content of the foam as well as optical features of the foam such as, for example, the pore size, for the purposes of assessing the foam. The compositions according to the invention have a large foam volume during the initial foaming. In practice, the initial foaming takes place within a relatively short period (from a few seconds to one minute). Typically, during initial foaming, a shower gel or a shampoo is spread and caused to foam by rubbing between hands, skin and/or hair. In the laboratory, the foaming behavior of an aqueous surfactant solution can be assessed e.g. by agitating the solution within a comparatively short time period by means of stirring, shaking, pumping, bubbling through a gas stream or in another way. Subjective assessment of the foam sensory property can be made by test subjects. For this purpose, aspects such as creaminess, elasticity, moldability of the foam may be assessed.

Good skin and mucosa compatibility. These can be detected by in vitro methods known to those skilled in the art (e.g. RBC or HET-CAM) and also by test subjects (e.g. patch test).

Outstanding care performance on skin and hair. This can be assessed, for example in test subjects by reference to subjective skin feel (smoothness, dryness etc.) or haptics and feel of the treated hair. Mechanical measurement methods, such as combability of the hair, for example can also be used.

Good storage stability. This is then the case if the aqueous compositions do not exhibit any visible (e.g. cloudiness, discoloration, phase separation) or measurable (e.g. pH, viscosity, active substance content) changes over a period of several weeks.

Good applicability and processability. The compositions can be dissolved rapidly and without supply of heat on introducing water.

Good clear solubility and transparency. The aqueous surfactant compositions do not have a tendency to precipitation or cloudiness.

Sufficiently high viscosity, which is understood in the context of the present invention to mean a value of 1000 mPas or higher (measured with a Brookfield RV laboratory rheometer at 23° C., 12 rpm, spindle set RV 02 to 07 (spindle choice depending on viscosity range)). As is known, "mPas" means millipascal seconds.

Good cleaning performance. The aqueous surfactant compositions are suitable for removing and emulsifying soiling, especially fat or oil-containing soiling, from solid or textile surfaces.

The Compounds (A)

The compounds (A), which are referred to within the context of the present invention as alpha-sulfo fatty acid disalts, are obligatory for the aqueous surfactant compositions according to the invention. They have the formula (I) specified above $$R^1CH(SO_3M^1)COOM^2 \qquad (I),$$

in which the radical $R^1$ is a linear or branched alkyl or alkenyl radical having 6 to 18 carbon atoms and the radicals $M^1$ and $M^2$—independently of one another—are selected from the group comprising H, Li, Na, K, Ca/2, Mg/2, ammonium and alkanolamines. In this case, the conditions specified above apply to the compounds (A):

the fraction of the compounds (A) in which the radical $R^1$ is an alkenyl radical—based on the total amount of the compounds (A) in the aqueous surfactant compositions—is 3% by weight or less and the fraction of the compounds (A) in which the radical $R^1$ is a decyl or dodecyl radical—based on the total amount of the compounds (A)—is 70% by weight or more.

If the radicals $M^1$ or $M^2$ are alkanolamines, preference is given to monoethanolamine, diethanolamine, triethanolamine and monoisopropanolamine.

In a preferred embodiment, the radical $R^1$ in the formula (I) is a saturated, linear alkyl radical having 10 to 16 carbon atoms, where with regard to the compounds (A) it is the case that the fraction of the compounds (A) in which the radical $R^1$ is a decyl and/or a dodecyl radical—based on the total amount of the compounds (A)—is 90% by weight or more.

The radicals $M^1$ and $M^2$ in formula (I) are preferably selected from the group comprising H (hydrogen) and Na (sodium).

The compounds (A) can be prepared by all methods known appropriately to the person skilled in the art. A particularly preferred method of preparation here is the sulfation of the corresponding carboxylic acids. Here, the corresponding carboxylic acid and in particular the corresponding fatty acids are reacted with gaseous sulfur trioxide, the sulfur trioxide being used preferably in an amount such that the molar ratio of $SO_3$ to fatty acid is in the range from 1.0:1 to 1.1:1. The crude products obtained in this way, which are acidic sulfation products, are then partially or completely neutralized, preference being given to complete neutralization with aqueous NaOH. If desired, it is also possible to undertake purification steps and/or a bleaching (for adjusting the desired pale color of the products).

In a particularly preferred embodiment, the compounds (A) are used in technical-grade form. This means that the corresponding carboxylic acids, in particular native fatty acid, are sulfated with gaseous sulfur trioxide, as a result of which, following partial or complete neutralization of the resulting acidic sulfation products, a mixture of the compounds (A), (C) and (D) results. By virtue of corresponding adjustments of the reaction parameters (in particular molar ratio of carboxylic acid and sulfur trioxide, and also reaction temperature) it is possible to control the ratio of the compounds (A), (C) and (D). The compounds (C) and (D) are described below in the chapter "Preferred embodiments".

In the context of the present invention, preference is given to those technical-grade mixtures of alpha-sulfo fatty acid disalts which have the following composition:

the content of (A) is in the range from 60 to 100% by weight,
the content of (C) is in the range from 0 to 20% by weight,
the content of (D) is in the range from 0 to 20% by weight, with the proviso that the sum of the components (A), (C) and (D) in this mixture is 100% by weight.

The Compounds (B)

The compounds (B), which are referred to in the context of the present invention as alkanolamides, are obligatory for the aqueous surfactant compositions according to the invention. The compounds (B) are selected from the group of compounds of general formula (IIa), (IIb) and (IIc), $$R^{13}\text{—CO—}NR^{14}R^{15} \qquad (IIa)$$

$$R^{13}\text{—CO—}NR^{14}R^{16} \qquad (IIb)$$

$$R^{13}\text{—CO—}NR^{14}R^{17} \qquad (IIc)$$

wherein the radical $R^{13}$ in compounds (IIa) is a linear or branched alkyl radical having 6 to 18 carbon atoms and the radicals $R^{14}$ and $R^{15}$—independently of each other—are a linear or branched hydroxyalkyl group having 1 to 4 carbon atoms;

wherein the radical $R^{13}$ in compounds (IIb) is a linear or branched alkyl radical having 6 to 18 carbon atoms, the radical $R^{14}$ is a linear or branched hydroxyalkyl group having 1 to 4 carbon atoms and the radical $R^{16}$ is hydrogen;

and wherein the radical $R^{13}$ in compounds (IIc) is a linear or branched alkyl radical having 6 to 18 carbon atoms, the radical $R^{14}$ is a linear or branched hydroxyalkyl group having 1 to 4 carbon atoms and the radical $R^{17}$ is an alkyl group having 1 to 4 carbon atoms.

It should be noted explicitly that it is logically self-evident to the person skilled in the art that the designation "branched" in the expression "linear or branched hydroxyalkyl group having 1 to 4 carbon atoms" naturally may refer only to hydroxyalkyl groups having at least three carbon atoms since corresponding radicals having 1 or 2 carbon atoms cannot comprise any branching. The expression "linear or branched hydroxyalkyl group having 1 to 4 carbon atoms" is therefore to be seen as a linguistic simplification.

The compounds (B) can be prepared by all of the methods known appropriately to the person skilled in the art. For example, by reaction of fatty acids, fatty acid methyl esters or fatty acid glycerides with alkanolamines.

In a preferred embodiment, the compounds (B) are selected from the alkanolamides with the INCI names Cocamide MEA, Cocamide DEA, Cocamide MIPA, Lauramide MEA, Lauramide DEA or Lauramide MIPA.

Preferred Embodiments

In one embodiment, the aqueous surfactant compositions according to the invention comprise, besides the compounds (A), (B) and water, additionally one or more compounds (C) of general formula (III)

$$R^4COOM^5 \qquad (III)$$

In the formula (III), the radical $R^4$ is a linear or branched alkyl or alkenyl radical having 7 to 19 carbon atoms and the radical $M^5$ is selected from the group comprising H, Li, Na, K, Ca/2, Mg/2, ammonium and alkanolamines. In this connection, particularly preferred alkanolamines are monoethanolamine, diethanolamine, triethanolamine and monoisopropanolamine.

In one embodiment, the aqueous surfactant compositions according to the invention comprise, besides the compounds (A), (B) and water, additionally one or more inorganic salts of sulfuric acid (D) of general formula (IV)

$$(M^6)_2SO_4 \qquad (IV)$$

wherein $M^6$ is selected from the group comprising Li, Na, K, Ca/2, Mg/2, ammonium and alkanolamine. In this connection, particularly preferred alkanolamines are monoethanolamine, diethanolamine, triethanolamine and monoisopropanolamine.

In a preferred embodiment, the aqueous surfactant compositions according to the invention comprise the compounds (A), (B), (C) and (D). It is particularly preferable in this case if the radicals $M^1$ and $M^2$ of the compounds (A), the radical $M^5$ of the compounds (C) and the radical $M^6$ of the compounds (D) are selected from the group comprising H (hydrogen) and Na (sodium).

In one embodiment, the aqueous surfactant compositions according to the invention comprise, besides the compounds (A), (B) and water, additionally one or more compounds (F) of general formula (VI)

$$R^6CH_2\text{—}CO\text{—}CHR^7(SO_3M^8) \qquad (VI),$$

in which the radicals $R^6$ and $R^7$—independently of each other—are a linear or branched alkyl radical having 6 to 18 carbon atoms and the radical $M^8$ is selected from the group comprising H, Li, Na, K, Ca/2, Mg/2, ammonium and alkanolamines. In this connection, particularly preferred alkanolamines are monoethanolamine, diethanolamine, triethanolamine and monoisopropanolamine.

In the context of the present invention, the compounds (F) are referred to as monosulfoketones.

In a preferred embodiment, the radicals $R^6$ and $R^7$ in the formula (VI)—independently of each other—are a saturated, linear radical having 10 to 16 carbon atoms, where, with regard to the compounds (F) it is the case that the fraction of the compounds (F) in which the radicals $R^6$ and $R^7$ are a decyl and/or a dodecyl radical—based on the total amount of the compounds (F)—is 70% by weight or more and preferably 90% by weight or more. The radical $M^8$ in formula (VI) is preferably selected from the group comprising H (hydrogen) and Na (sodium).

In one embodiment, the aqueous surfactant compositions according to the invention comprise, besides the compounds (A), (B) and water, additionally one or more compounds (G) of general formula (VII)

$$(SO_3M^9)R^8CH\text{—}CO\text{—}CHR^9(SO_3M^{10}) \qquad (VII),$$

in which the radicals $R^8$ and $R^9$—independently of each other—are a linear or branched alkyl radical having 6 to 18 carbon atoms and the radicals $M^9$ and $M^{10}$—independently of each other—are selected from the group comprising H, Li, Na, K, Ca/2, Mg/2, ammonium and alkanolamines. In this connection, particularly preferred alkanolamines are monoethanolamine, diethanolamine, triethanolamine and monoisopropanolamine.

In the context of the present invention, the compounds (G) are referred to as disulfoketones.

In a preferred embodiment, the radicals $R^8$ and $R^9$ in the formula (VII)—independently of each other—are a saturated, linear radical having 10 to 16 carbon atoms, where, with regard to the compounds (G) it is the case that the fraction of the compounds (G) in which the radicals $R^8$ and $R^9$ are a decyl and/or a dodecyl radical—based on the total amount of the compounds (G)—is 70% by weight or more and preferably 90% by weight or more. The radicals $M^9$ and $M^{10}$ in formula (VII) are preferably selected from the group comprising H (hydrogen) and Na (sodium).

The preparation of the compounds (F) and (G) is not subject to any particular restrictions and they can be prepared by all methods known to those skilled in the art.

In one embodiment, the compounds (F) and (G) are prepared by sulfonation of the corresponding ketones with gaseous sulfur trioxide, as described in the German published specification DE-A-42,20,580.

In another embodiment, the preparation of the compounds (F) and (G) starts from fatty acids. In this case, the sulfation of liquid fatty acids with gaseous sulfur trioxide is conducted such that, in addition to disalts (A), the compounds (F) and (G) are also formed in this case, which can be accomplished as a result of carrying out the sulfation as follows: the ratio of fatty acid raw materials, which may also be used in the form of mixtures of fatty acids of different chain length, to sulfur trioxide is adjusted so that 1.0 to 1.5 mol and especially 1.0 to 1.25 mol of $SO_3$ are used per mole of fatty acid(s). The fatty acids are introduced into the reactor at a reservoir temperature in the range of 70 to 100° C. After the sulfation, the resulting liquid sulfation product is maintained and aged at this temperature for 5 to 20 minutes in a temperature-controlled post-reaction coil. Neutralization is then effected with an aqueous base, preferably sodium hydroxide, generally in a pH range of 5 to 10, especially 5 to 7. Subsequently, an acidic bleaching—the pH here is adjusted to a value of 7 or less—may be carried out with hydrogen peroxide.

In one embodiment, the aqueous surfactant compositions according to the invention comprise the compounds (A), (B)

and (F). It is particularly preferable in this case if the radicals $M^1$ and $M^2$ of the compounds (A) are selected from the group comprising H (hydrogen) and Na (sodium). The proviso applies in this case that the amount of the compounds (A) must be greater than the amount of the compounds (F).

In one embodiment, the aqueous surfactant compositions according to the invention comprise the compounds (A), (B) and (G). It is particularly preferable in this case if the radicals $M^1$ and $M^2$ of the compounds (A) are selected from the group comprising H (hydrogen) and Na (sodium). The proviso applies in this case that the amount of the compounds (A) must be greater than the amount of the compounds (G).

In one embodiment, the aqueous surfactant compositions according to the invention comprise the compounds (A), (B), (F) and (G). It is particularly preferable in this case if the radicals $M^1$ and $M^2$ of the compounds (A) are selected from the group comprising H (hydrogen) and Na (sodium). The proviso applies in this case that the amount of the compounds (A) must be greater than the sum total of the amount of the compounds (F) and (G).

In one embodiment, the aqueous surfactant compositions according to the invention comprise the compounds (A), (B), (C), (D) and (F). It is particularly preferable in this case if the radicals $M^1$ and $M^2$ of the compounds (A), the radical $M^5$ of the compounds (C) and the radical $M^6$ of the compounds (D) are selected from the group comprising H (hydrogen) and Na (sodium). The proviso applies in this case that the amount of the compounds (A) must be greater than the amount of the compounds (F).

In one embodiment, the aqueous surfactant compositions according to the invention comprise the compounds (A), (B), (C), (D) and (G). It is particularly preferable in this case if the radicals $M^1$ and $M^2$ of the compounds (A), the radical $M^5$ of the compounds (C) and the radical $M^6$ of the compounds (D) are selected from the group comprising H (hydrogen) and Na (sodium). The proviso applies in this case that the amount of the compounds (A) must be greater than the amount of the compounds (G).

In one embodiment, the aqueous surfactant compositions according to the invention comprise the compounds (A), (B), (C), (D), (F) and (G). It is particularly preferable in this case if the radicals $M^1$ and $M^2$ of the compounds (A), the radical $M^5$ of the compounds (C) and the radical $M^6$ of the compounds (D) are selected from the group comprising H (hydrogen) and Na (sodium). The proviso applies in this case that the amount of the compounds (A) must be greater than the sum total of the amount of the compounds (F) and (G).

If desired, the aqueous surfactant compositions according to the invention can additionally comprise one or more further surfactants which, in structural terms, do not belong to the aforementioned compounds (A), (B), (D), (E), (F) or (G). These surfactants may be anionic, cationic, nonionic or amphoteric surfactants.

Use of the Compositions

A further subject matter of the invention is the use of the aforementioned compositions for cosmetic products, and also detergents and cleaners.

With regard to cosmetic products, particular preference is given here especially to those which are present in the form of hair shampoos, shower gels, soaps, syndets, washing pastes, washing lotions, scrub preparations, foam baths, oil baths, shower baths, shaving foams, shaving lotions, shaving creams and dental care products (for example toothpastes, mouthwashes and the like).

With regard to cleaners, of preference here are in particular products with a low pH for cleaning hard surfaces, such as bath and toilet cleaners and the like, and also for cleaning and/or fragrance gels for use in sanitary installations.

A preferred embodiment relates to the use of the aforementioned compositions for pearlescent concentrates.

The invention claimed is:

1. An aqueous surfactant composition comprising
one or more alpha-sulfo fatty acid disalt (A) of general formula (I)

$$R^1CH(SO_3M^1)COOM^2 \qquad (I),$$

in which the radical $R^1$ is a saturated, linear alkyl radical having 10 to 16 carbon atoms and the radicals $M^1$ and $M^2$, independently of one another, are selected from the group consisting of H, Li, Na, K, Ca/2, Mg/2, ammonium, and alkanolamine;

one or more alkanolamide (B) selected from the group of compounds of general formula (IIa), (IIb) and (IIc)

$$R^{13}CO—NR^{14}R^{15} \qquad (IIa)$$

$$R^{13}—CO—NR^{14}R^{16} \qquad (IIb)$$

$$R^{13}—CO—NR^{14}R^{17} \qquad (IIc),$$

wherein the radical $R^{13}$ in compounds (IIa) is a linear or branched alkyl radical having 6 to 18 carbon atoms and the radicals $R^{14}$ and $R^{15}$, independently of each other, are a linear or branched hydroxyalkyl group having 1 to 4 carbon atoms;

wherein the radical $R^{13}$ in compounds (IIb) is a linear or branched alkyl radical having 6 to 18 carbon atoms, the radical $R^{14}$ is a linear or branched hydroxyalkyl group having 1 to 4 carbon atoms, and the radical $R^{16}$ is hydrogen;

and wherein the radical $R^{13}$ in compounds (IIc) is a linear or branched alkyl radical having 6 to 18 carbon atoms, the radical $R^{14}$ is a linear or branched hydroxyalkyl group having 1 to 4 carbon atoms, and the radical $R^{17}$ is an alkyl group having 1 to 4 carbon atoms;

one or more compound (C) of general formula (III)

$$R^4COOM^5 \qquad (III),$$

in which the radical $R^4$ is a linear or branched alkyl or alkenyl radical having 7 to 19 carbon atoms and the radical $M^5$ is selected from the group consisting of H, Li, Na, K, Ca/2, Mg/2, ammonium, and alkanolamine;

one or more inorganic salt of sulfuric acid (D) of general formula (IV)

$$(M^6)_2SO_4 \qquad (IV),$$

wherein $M^6$ is selected from the group consisting of Li, Na, K, Ca/2, Mg/2, ammonium, and alkanolamine; and water, where the following provisos apply:

with regard to compound (A) it is the case that the fraction of the compound (A) in which the radical $R^1$ is a decyl or dodecyl radical, based on the total amount of the compound (A), is 90% by weight or more;

the content of compound (A) is in the range from 60 to 100% by weight based on the sum of compounds (A), (C), and (D) in the aqueous surfactant composition;

the content of compound (C) is in the range from more than 0 to 20% by weight based on the sum of compounds (A), (C), and (D) in the aqueous surfactant composition;

the content of compound (D) is in the range from more than 0 to 20% by weight based on the sum of compounds (A), (C), and (D) in the aqueous surfactant composition; and if the aqueous surfactant compositions comprise one or more ester sulfonate (E) of general formula (V)

$$R^2CH(SO_3M^7)COOR^3 \qquad (V),$$

in which the radical $R^2$ is a linear or branched alkyl or alkenyl radical having 6 to 18 carbon atoms and the radical $R^3$ is a linear or branched alkyl or alkenyl radical having 1 to 20 carbon atoms, where the radical $R^3$ can be an alkenyl radical or be branched only above 3 carbon atoms, and the radical $M^7$ is selected from the group consisting of Li, Na, K, Ca/2, Mg/2, ammonium, and alkanolamine, it is the case that the compound (A), based on the totality of the compounds (A) and (E), must be present to an extent of 50% by weight or more.

2. The composition according to claim 1, wherein the radicals $M^1$ and $M^2$ are selected from the group consisting of H (hydrogen) and Na (sodium).

3. The composition according to claim 1, wherein the composition additionally one or more monosulfoketone (F) of general formula (VI)

$$R^6CH_2\text{—}CO\text{—}CHR^7(SO_3M^8) \qquad (VI),$$

in which the radicals $R^6$ and $R^7$, independently of each other, are a linear or branched alkyl radical having 6 to 18 carbon atoms and the radical $M^8$ is selected from the group consisting of H, Li, Na, K, Ca/2, Mg/2, ammonium, and alkanolamine.

4. The composition according to claim 1, wherein the composition additionally one or more disulfoketone (G) of general formula (VII)

$$(SO_3M^9)R^8CH\text{—}CO\text{—}CHR^9(SO_3M^{10}) \qquad (VII),$$

in which the radicals $R^8$ and $R^9$, independently of each other, are a linear or branched alkyl radical having 6 to 18 carbon atoms and the radicals $M^9$ and $M^{10}$, independently of each other, are selected from the group comprising H, Li, Na, K, Ca/2, Mg/2, ammonium, and alkanolamine.

5. A composition according to claim 1 for use in cosmetic products and also detergents and cleaners.

6. A composition according to claim 1 for use in cosmetic products in the form of hair shampoos, shower gels, soaps, syndets, washing pastes, washing lotions, scrub preparations, foam baths, oil baths, shower baths, shaving foams, shaving lotions, shaving creams, and dental care products.

7. A composition according to claim 1 for use in products having a low pH for cleaning hard surfaces.

8. A composition as claimed in claim 1 for use as a pearlescent concentrate.

* * * * *